(12) United States Patent
Magnin

(10) Patent No.: US 7,736,694 B2
(45) Date of Patent: Jun. 15, 2010

(54) PROCESS FOR THE PREPARATION OF ANTIMICROBIAL POWDER COATING COMPOSITION

(75) Inventor: Olivier Magnin, Lausanne (CH)

(73) Assignee: Dupont Polymer Powders Switzerland Sarl

( * ) Notice: Subject to any disclaimer, the term of this patent is extended or adjusted under 35 U.S.C. 154(b) by 400 days.

(21) Appl. No.: 12/002,613

(22) Filed: Dec. 17, 2007

(65) Prior Publication Data

US 2008/0148994 A1 Jun. 26, 2008

Related U.S. Application Data

(60) Provisional application No. 60/876,812, filed on Dec. 22, 2006.

(51) Int. Cl.
*B05D 1/12* (2006.01)
*B05D 7/00* (2006.01)
*C09D 5/14* (2006.01)
*B29B 9/06* (2006.01)
*A61L 33/00* (2006.01)

(52) U.S. Cl. .................... 427/180; 106/15.05; 264/141; 427/2.1; 427/212

(58) Field of Classification Search ................. 427/212, 427/2.1
See application file for complete search history.

(56) References Cited

U.S. PATENT DOCUMENTS 6,093,407 A * 7/2000 Cummings et al. .......... 424/400
2005/0063246 A1 * 3/2005 Ponzielli ...................... 366/85

FOREIGN PATENT DOCUMENTS

WO WO 01/90259 11/2001

OTHER PUBLICATIONS

Rolf D. Joerger, Antimicrobial Activity: Film Contact Method—JIS Z2801, Dept. of Animal and Food Sciences, University of Delaware, Nov. 21, 2005.

* cited by examiner

*Primary Examiner*—Michael Cleveland
*Assistant Examiner*—Austin Murata
(74) *Attorney, Agent, or Firm*—Gann G Xu

(57) ABSTRACT

A process of preparation of an antimicrobial powder coating composition comprising the steps:
 a) transforming a natural antimicrobial agent into a salt-form and micronizing the resulting antimicrobial salt into powder,
 b) mixing at least one of the natural antimicrobial salt together with at least one amino-reactive thermoplastic binder resin,
 c) subjecting the mixture to a melt compounding process at a temperature in a range of 80 to 230° C., at a residence time period in a range of 5 to 60 seconds, using at least one co-rotating twin-screw extruder with a soft screw design having conveying elements offering a high D/d ratio and having mixing forward kneading block elements,
 d) cooling the extrudate, and
 e) micronizing into powder particles.

The process forms a powder coating composition containing a natural antimicrobial agent which results in high quality antimicrobial coatings showing a homogeneous distribution of the antimicrobial agent in the coating and a stable antimicrobial activity.

10 Claims, 3 Drawing Sheets

PROCESS FOR THE PREPARATION OF ANTIMICROBIAL POWDER COATING COMPOSITION

CROSS REFERENCE TO RELATED APPLICATIONS

This application claims the benefit of U.S. Provisional Application Ser. No. 60/876,812 filed on Dec. 22, 2006 which is hereby incorporated by reference.

FIELD OF THE INVENTION

The invention is directed to a process of preparation of a powder coating composition comprising antimicrobial agents for coating surfaces of metal parts used in food processing equipments, healthcare, transportation and paper industry.

DESCRIPTION OF PRIOR ART

Public concern about the health hazards arising from microorganisms, such as, bacteria, fungi, viruses and the like is high. Also, it is desirable to prevent biological defacement of object surfaces due to the growth of microorganisms.

Thus, a number of efforts have been undertaken to produce objects with the ability to kill or inhibit the growth or reproduction of microorganisms, which is termed "antimicrobial activity" herein. Anti-microbial agents in final coatings including paint and powder coatings are known.

U.S. Pat. No. 6,093,407 discloses an antimicrobial powder coating composition where the antimicrobial agent is homogeneously dispersed within the particles of the resin based powder. The components can be blended together, fed then, for example, into an extruder, heated and melted. The solid extrudate can be processed after cooling into a coating powder. WO 01/90259 discloses a technique by kneading an antibacterial agent in a polyamide resin, and the kneaded product is pulverized into finer particles to produce a powder paint composition. However, none of the existing and commonly used techniques of heat-melting and compounding guarantees the avoidance of degradation of the antimicrobial agent, especially natural antimicrobial agent, and, therefore, the avoidance of uneven antimicrobial activity or non-activity of the antimicrobial agent on the powder coated substrate surface.

Techniques to avoid such non-activities of antimicrobial powder coatings refer to multilayer processes, for example, to dual-layer processes where a powder coating is applied first onto the substrate surface. Then the antimicrobial agent is applied, for example, by dipping the powder coated substrate into a dispersion or solution of the antimicrobial agent.

Therefore, there is a need for improved powder coatings that exhibit a stable antimicrobial activity and high adhesion when applied to substrates as well as an easy usable powder coating process. Additionally, the improved antimicrobial powder coatings should gain a substantial acceptance by the public as being non-allergenic coatings.

SUMMARY OF THE INVENTION

The present invention provides a process of preparation of an antimicrobial powder coating composition comprising the steps:

a) transforming a natural antimicrobial agent into a salt-form and micronizing the resulting antimicrobial salt into powder, b) mixing at least one of the natural antimicrobial salt together with at least one amino-reactive thermoplastic binder resin, c) subjecting the mixture to a melt compounding process at a temperature in a range of 80 to 230° C., at a residence time period in a range of 5 to 60 seconds, using at least one co-rotating twin-screw extruder with a soft screw design having conveying elements offering a high D/d ratio and having mixing forward kneading block elements, d) cooling the extrudate, and e) micronizing into powder particles.

The process according to the invention provides a powder coating composition containing a natural antimicrobial agent which results in high quality antimicrobial coatings showing a homogeneous distribution of the antimicrobial agent in the coating and a stable antimicrobial activity as well as a high adhesion on the substrate surface. The powder coating composition prepared by the process according to the invention can be used as mono-layer antimicrobial coating, and can therefore be used as alternative to the above mentioned dual-layer coating process.

DETAILED DESCRIPTION OF THE INVENTION

Figure 1:
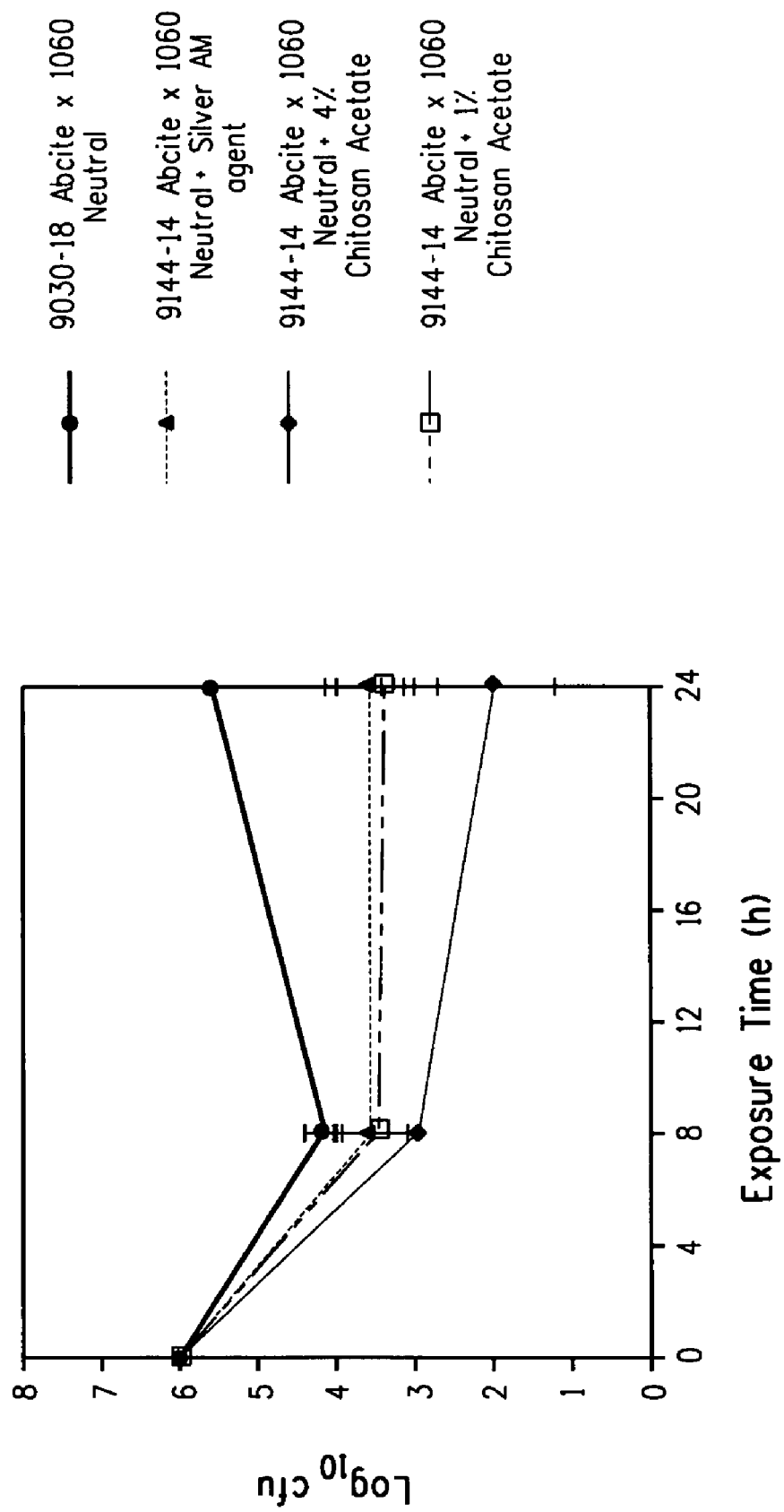
FIG. 1 is a graph that shows the effect of Abcite® coated surface on *e. Coli* 25922.

The features and advantages of the present invention will be more readily understood, by those of ordinary skill in the art, from reading the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

All patents, patent applications and publications referred to herein are incorporated by reference in their entirety.

The powder coating composition prepared by the process according to the invention may be applied to the substrate so that bacterial or fungal contact with the coating either kills them or at least inhibits their growth. For example, in some embodiments, antimicrobial activity with respect to *Staphylococcus aureus, Escherichia coli, L. monocytogenes* Scott A, *Bacillus subtillus, Streptococcus faecadis, Salmonella typhinurium, Pseudomonas aeruginosa*, and other Gram positive and Gram negative bacteria may be achieved. The growth of certain higher organisms like algae, fungi, filamentous fungi (*Aspergillus, Aureobasidium, Botrytis, Ceratostomella, Cuvularia, Fusarium* and *Penicillium* species), yeast and also, some viruses may also be inhibited.

Potential applications for these improved powder coatings may include, for example, food preparation areas, restrooms, hospitals, garbage disposals, stockyard areas, animal feed troughs, schools, kitchens, swimming pool areas, dishwashers, automobile fixtures, public access fixtures, public seating, public transportation fixtures, toys, and other industrial, agricultural, commercial or consumer products, made from, for example, plastics, metal, glass.

Particularly the process according to the invention is suitable for the coating of metallic substrates.

The process according to the invention refers to mixing at least one natural antimicrobial agent together with at least one amino-reactive thermoplastic binder resin.

The amino-reactive thermoplastic binder resin may be one or more of the thermoplastic resins including those based on functionalized polyolefines, ionomer resins, polyesters, polyamides, cellulosic polymers, polysiloxane and/or polyurethane resins, in a preferred range of 70 to 99.9 wt %, especially preferred in a range of 80 to 99 wt % based on the total weight of the powder coating composition. Examples for amino-reactive thermoplastic resins are ethylene copolymers resins—such as ethylene (meth)acrylic acid, ethylene (meth)acrylate-ion, ethylene vinyl acetate, ethylene acrylate-, maleic anhydride-grafted polyethylenes and polypropylenes, polyamides—such as aliphatic and aromatic polyamides (aramides)-, polyesters—such as hydrolyzed or terephtalates polyesters, especially preferred resins are ethylene (meth)acrylic acid, ethylene (meth)acrylate and ethylene vinyl acetate. Suitable amino-reactive thermoplastic binder resins are, for example, Abcite®, Flamulit®, Surlyn®, Nucrel®, Bynel®, Fusabond®, Elvax®, Nomex®, Kevlar®, Sorona®, Mylar® (DuPont de Nemours Intl), Coolmax® (Invista).

The natural antimicrobial agent, used for viral, bacterial, fungal and parasites challenges, as well as overall immune support, may be one or more of known natural antimicrobial agents, such as, chinokitiol, chitin, chitosan, olive leaf extract in a preferred range of 0.1 to 20 wt %, especially preferred in a range of 1 to 10 wt % based on the total weight of the powder coating composition. Preferred is the use of chitin and chitosan.

With regard to step a) of the process according to the invention the natural antimicrobial agent may be dissolved in an acid solution, for example, at room temperature, for example, 18 to 25° C., or at increased temperature in a range of, for example, 30 to 40° C. Acids which may be used are aliphatic mono-carboxylic acids with a carbon number of, for example, C1-C4, for example, acetic acid, propanoic acid, in a preferred range of 1 to 20 wt %, especially preferred in a range of 2 to 10 wt % based on total weight of the solution. The obtained natural antimicrobial salt is then precipitated by adding, for example, a non-solvent, for example, alcohols or ketones. Preferred non-solvents are methanol, ethanol, isopropanol or acetone. After filtration by means known by the art, for example, under vacuum or at atmospheric pressure, and after washing with, for example, inert organic solvents, for example, alcohols or ketones, the natural antimicrobial salt is dried and then micronized into a powder, for example, by using an attrition or an impact milling process known at a person skilled in the art, for example, at room temperature, for example, 18 to 25° C. The resulting powder may be classified by using, for example, mechanical or wind sieving techniques.

The mixing step b) of at least one natural antimicrobial agent with at least one amino-reactive thermoplastic binder resin may be proceed, for example, by a dry-mixing process, for example, in a low intensity mixer.

The subjecting step c) of the melt compounding process may be proceed at a temperature in a preferred range of 90 to 150° C., especially preferred in a range of 100 to 120° C., at a residence time period in a preferred range of 5 to 40 seconds, especially preferred in a range of 10 to 25 seconds. The melt compounding process may be carried out in compounding devices, such as a co-rotating twin-screw extruder with a soft screw design, using conveying and mixing elements. Preferred conveying elements are conveying elements offering a high D/d ratio. The D/d ratio describes the degree of filling capacity of the extruder. The term D means the external screw diameter and the term d means the internal screw diameter. A high D/d ratio is, for example, in the range of 1.50 to 1.55. Preferred mixing elements are forward kneading block elements ensuring an excellent conveying effect.

The cooling step d) consists in cooling down the resulted extrudate using methods known in the art, for example, in a cold atmosphere or liquid, such as, water, whereby a crystallized extrudate is obtained. The cooling may be proceed in a preferred temperature range of 5 to 20° C., especially preferred in a range of 10 to 15° C., at a residence time period in a preferred range of 10 to 40 seconds, especially preferred of 20 to 30 seconds. The solid extrudate is then dried by air.

After granulating the extrudate into suitable sized compound granules or pellets by using methods known in the art the micronizing step e) follows by cooling the compounded granules at low temperatures, in a preferred range of −120 to −200° C., especially preferred in a range of −140 to −180° C. with, for example, liquid nitrogen. The brittle extra-cold granules are then fed into a grinder that reduces the granules to fine particles by using, for example, the impact or attrition milling process known by a person skilled in the art. The milling technique is selected in function of the ductility of the compound pellet to grind, as known at a person skilled in the art, and in function of the final particle size distribution targeted. Examples are the known impact technique, for example for friable materials, and the known attrition technique using rotary equipment for soft to medium-hard materials. The resulting fine powder may be classified to the desired grain size, for example, to a particle size distribution in a range of 20 and 500 micrometers, by using known sieving techniques.

The coating composition useable according to the process of the invention may also contain one or more liquid or solid antimicrobial agents different from the natural antimicrobial agent, in a content from 0.1 percent to 5 percent by weight of the total composition, for example, phthalimides, acetamides, phthalonitriles, hydroxy benzoates, isothiazolinones, nitropropane diols, carbamates, methyl ureas, benzimidazoles, salicylanilides, mercury acetates, organozinc compounds, metals, such as, silver, copper and zinc, and ions of such metals. The liquid antimicrobial agents may be incorporated within the powder coating particle using methods known in the art, for example, under the use of supercritical fluids.

The powder coating composition useable in this invention may contain 0 to 20 wt % of at least one pigment and/or filler and/or extender, for example, transparent, color-imparting and/or special effect-imparting pigments and/or extenders known in the art. Suitable color-imparting pigments are any conventional coating pigments of an organic or inorganic nature. Examples of inorganic or organic color-imparting pigments are titanium dioxide, micronized titanium dioxide, carbon black, azopigments, and phthalocyanine pigments. Examples of special effect-imparting pigments are metal pigments, for example, made from aluminum, copper or other metals, interference pigments, such as, metal oxide coated metal pigments and coated mica. Examples of usable fillers and/or extenders are silicon dioxide, silicate, such as, aluminum silicate, barium sulfate, calcium carbonate, magnesium carbonate and double carbonates thereof.

The powder coating composition according to the invention may contain the constituents and additives conventional in powder coating technology, such as, flow-control agents, flatting agents, catalysts, stabilizers. The additives are used in a range of 0.01 to 10 wt %, preferred in a range of 0.1 to 5 wt % based on the total weight of the powder coating composition.

As a stabilizer the use of thermal and/or UV stabilizers is preferred.

The powder coating composition of this invention may be applied onto the substrate by electro-spraying, pneumatic spraying, thermal or flame spraying, or fluidized bed coating methods, all of which are known to those skilled in the art.

For example, the procedure recommends a pre-treatment step where steel or metal surfaces have to be free of rust, grease or other contaminants. After degreasing, mechanical or chemical treatment may be possible. For a better adhesion of the coatings, a sand or grit blasted surface can be used.

In certain applications, the substrate to be coated may be pre-heated before the application of the powder, for example, in a range of 80 to 250° C., preferred in a range of 160 to 240° C., especially preferred in a range of 200 to 220° C., dependent on the kind of the substrate. For example, gas is commonly used for various heating steps, for example air heating, but other methods, e.g., microwaves, IR or NIR are also known.

With regard to fluidized bed coating methods, the hot substrate is dipped, for example, into a fluidized bed containing the powder composition prepared by the process according to the invention, for 1 to 8 seconds and kept continuously in motion. The coated substrate is then removed and, for example, shaken to remove excess powder. Fluidised bed temperatures should be maintained below 50° C. Filtered air may be used to fluidise the powder in the bed.

The post-heating or the curing follows to finish the film forming on the substrate by heating the coated substrate at a temperature in a range of 100 to 250° C., preferred of 180 to 240° C., especially preferred in a range of 200 to 220° C., depending on the type of the substrate and the substrate thickness. The time may be, for example, 1 to 20 minutes. The heating may be done by gas or air heating, e.g., in an oven, and/or infrared (IR) or near infrared (NIR) radiation as known in the art, to finish the film forming on the substrate and to cure the film.

Finally, the coated substrate is cooled down to room temperature, for example, by air or by water quenching.

The coating composition may be applied to the substrate surface as a mono-layer coating. It may also be applied as coating layer in a multi-layer film build.

Preferably the coating composition may be applied as a mono-layer coating directly onto the substrate surface.

The applied powder coating compositions according to the invention can be coated with at least one coating layer, e.g., a top coat which can be each kind of top coats, e.g., a UV powder top coat or a liquid top coat.

Dual curing methods are also possible if desired. Dual curing means a curing method where the applied composition can be cured both by high energy radiation and by thermal curing methods known by a skilled person. High energy radiation means UV (ultraviolet) radiation or electron beam radiation, carried out, for example, in a belt unit fitted with one or more UV-radiation emitters or with one or more UV-radiation emitters positioned in front of the object to be irradiated, or the area to be irradiated, or the substrate to be irradiated and/or the UV-radiation emitters are moved relative to one another during irradiation. The powder coating composition according to the invention may therefore contain photoinitiators in quantities of, e.g., 0.1 to 7 weight-%, relative to the total of resin solids and photoinitiators, for example, benzoin and derivatives, acetophenone and derivatives, hydroxyalkyl phenones and acyl phosphine oxides.

The present invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. As a result, the present invention is not limited by the illustrative examples set forth herein below, but rather is defined by the claims contained herein below.

The following Examples illustrate the invention.

EXAMPLES

Example 1

Preparation of a Powder Coating Composition According to the Invention and Application Powder Coating Formulation 1:

| | |
|---|---|
| Ethylene (meth)acrylate resin | 97.9 |
| Chitosan Acetate Powder | 1.0 |
| UV and thermal stabilizer | 0.7 |
| Flow agent | 0.4 |

Powder Coating Formulation 2:

| | |
|---|---|
| Ethylene (meth)acrylate resin | 94.9 |
| Chitosan Acetate Powder | 4.0 |
| UV and thermal stabilizer | 0.7 |
| Flow agent | 0.4 |

The natural antimicrobial agent is first dissolved at room temperature in an acetic acid solution in a range of 5 to 10 wt % based on total weight of the solution. The Chitosan acetate is then precipitated by adding isopropanol and is then isolated by paper-filtration under vacuum at room temperature. The slurry is washed by acetone and then dried in a hot air oven at 40° C. during 24 hours. The dry and brittle Chitosan acetate is then milled and classified at 400 micrometers using a standard mill at room temperature.

The dry Chitosan acetate powder is then dry mixed with ethylene (meth)acrylate resin by a low intensity mixer. The mixture is intimately mixed by soft melt compounding process. The compounding temperature is comprised between 100 and 120° C. at a residence time comprised between 10 and 25 seconds. The melt compounding process is carried out in a co-rotating twin-screw extruder with a specific soft screw design, using conveying elements offering a D/d ratio in the range of 1.52 to 1.55 and using mixing forward kneading block elements. The extrudate is then cooled down in cold water (10-15° C.) at a residence time of 10 to 20 seconds and therefore optimally crystallized. The solid extrudate is then dried and granulated into the suitable sized granules by a rotary cutter. Finally, the compound granules are cooled down to (−140 to −180° C.) with liquid nitrogen. The brittle extra-cold granules are then fed into a grinder that reduces the granules to fine particles by using the attrition milling process. The resulting fine powder is classified to the desired particle size distribution, comprised between 50 and 400 micrometers, by using the mechanical sieving technique.

The resulted powder coating composition is then applied onto steel substrates following the dipping into fluidized bed method. The steel substrates are cleaned in order to be free of rust, grease or other contaminants.

The steel substrate is pre-heated in a hot air oven at 220° C. during 8 minutes. The hot object is then dipped into a fluidized bed containing the powder composition prepared by the process according to the invention during 4 seconds and kept continuously in motion. The coated specimen is then removed and shaken gently for a couple of seconds to remove excess powder. In order to finish the film forming on the substrate, the coated specimen is post-heated at 220° C. during 3 minutes. Finally, the coated specimen is air-cooled down to room temperature. As a result, the steel specimen is coated following a one-pass coating.

Example 2

Testing of the Coatings

TABLE 1

| | Adhesion to substrate[1] | Antimicrobial Activity of the coating (log reduction)[2] | Abrasion Resistance[3] | Impact Resistance[4] | Salt Spray Resistance (scibed plate)[5] | Accelerated Weathering (UV)[6] |
|---|---|---|---|---|---|---|
| Formulation 2 | >7 [n(mm²)] | −3.90 vs E. Coli 25922<br>−3.54 vs L. monocytogenes Scott A<br>−4.60 vs S. aureus 6530 | <7 mg | >8 [J] | <3 mm after 1'000 hours | >2'000 hours (no microcracks) |

[1]Adhesion: ASTM D 4541
[2]Antimicrobial Activity: Film Contact Method - JIS Z2801, performed by Rolf D. Joerger, Dept. of Animal and Food Sciences, University of Delaware, Nov. 21, 2005
[3]Abrasion Resistance (Taber, 1000 g, CS17): ASTM D 4060
[4]Impact (direct failure): ASTM D 2794
[5]Salt Spray: ASTM B 117
[6]Accelerated Weathering (UV + condensation): ASTM G53

Antimicrobial Activity

Effect of Washed Plates Coated with Natural Antimicrobial Chitosan Acetate on *E. coli* 25922, *Listeria monocytogenes* Scott A, and *Staphylococcus aureus* 6530.

Methods

After the first test, the surfaces of the plates were wiped clean with 70% ethanol followed by soaking overnight in 200 mL of tap water. The plates were cleaned a second time with 70% ethanol then soaked in sterile distilled water for 6 h. The plates were dried in the biohood overnight.

The assay was done using the "Film Contact Method—JIS Z2801" as revised by the Milliken Microbiology Lab with minor modifications.

a. Bacteria

The three test strains were grown in TSB (Tryptic Soy Broth) overnight at 37° C. with shaking. Ten µL of each culture were pipetted into 100 mL of Exposure Solution (0.2% Nutrient Broth; composition per L: 60 mg beef extract, 200 mg peptone, 100 mg NaCl) to achieve a bacteria density of between 105 to 106 colony forming units (cfu)/mL. The actual counts were determined by serial dilution of the bacteria mixture and plating onto three selective media (MacConkey Agar for *E. coli*; PALCAM for *L. monocytogenes*; Difco Chapman Stone Medium for *S. aureus*) and on non-selective TSA (Tryptic Soy Agar).

b. Exposure of Bacteria to Surfaces

The Chitosan Acetate coated plates were placed into sterile, square petridishes. (Three plates of each type were used for the assays.) Two-hundred-seventy-five µL of the Exposure solution containing the bacteria were spotted onto the surface of the Chitosan Acetate coated plates, and a 4×4.5 cm cover film prepared from stomacher bags (Seward Model 400 bags) was carefully lowered onto the spots. If necessary, slight pressure was used to distribute the liquid fully under the cover film. The petridishes were placed in a plastic bag containing a moist paper towel to provide a humid atmosphere and kept at room temperature for 24 h.

c. Recovery of Bacteria from Chitosan Acetate Coated Plates

The Chitosan Acetate coated plate was moved to an upright position using sterile forceps. The cover film was removed and placed in the bottom of the Petridish. Ten mL of Wash Solution (Tryptic Soy Broth, 0.7% Tween 80 and 0.01% L-cysteine) were pipetted onto the surface of the Chitosan Acetate coated plate. The wash solution was collected again and used to rinse the surface once more. A total of 10 rinses were done. The Chitosan Acetate coated plate was removed and the previously submerged cover film was rinsed three times.

d. Enumeration of Bacteria

The rinse solution containing the recovered bacteria was serially diluted and plated onto the selective media and the TSA. Colonies on MacConkey Agar and on TSA were counted after 24 h, those on PALCAM and Chapman Stone Medium were counted after 48 h. The number of cfus initially spotted onto the surfaces was calculated by multiplying the count per mL with 0.275. The number of bacteria present after 24 h of exposure to the plates was calculated by multiplying the counts per mL by 10 to account for the dilution in the rinse solution.

e. Selection of Bacteria

The three bacteria used, *E. Coli* 25922, *Staphylococcus aureus* 6530 and *Listeria monocytogenes* Scott A, are good indicators of the probability of future success with killing other microorganisms, since they represent both two types of bacteria (Gram positive and Gram negative) and slightly different susceptibilities to antimicrobial agents. It is expected to find more microbes that are easily killed by this technology, and others that are less susceptible.

f. Selection of Coatings

The three following coatings were tested against the three above-mentioned bacteria, according to the "Film Contact Method—JIS Z2801":

Powder Coating Formulation 1: Abcite® X1060+1% Chitosan Acetate

Powder Coating Formulation 2: Abcite® X1060+4% Chitosan Acetate

Commercial Silver Powder Coating: Abcite® X1060+Silver AM agent

Figure 2:
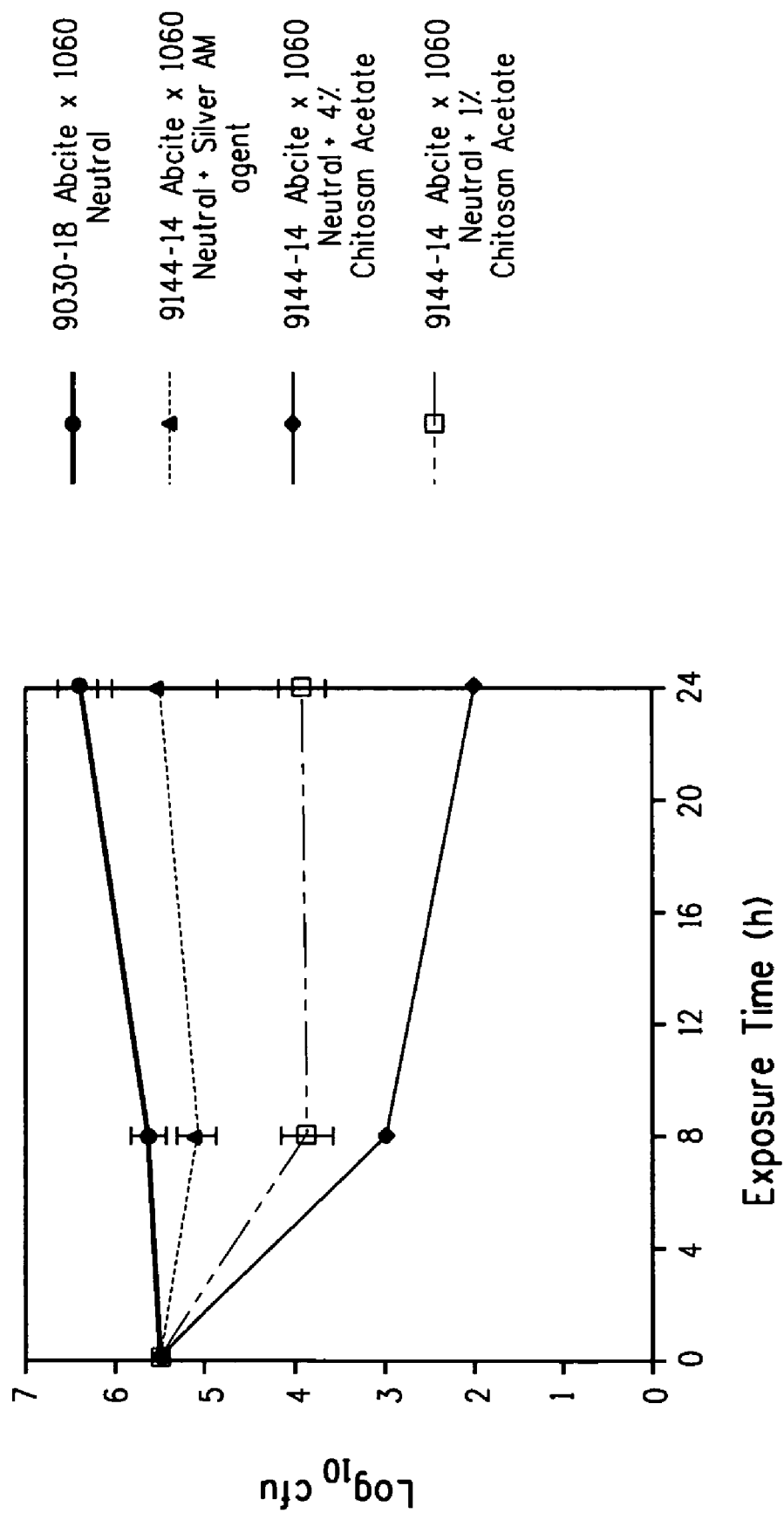
FIG. 2 is a graph that shows the effect of Abcite® coated surface on *Staphylococcus aureus* 6530.
Figure 3:
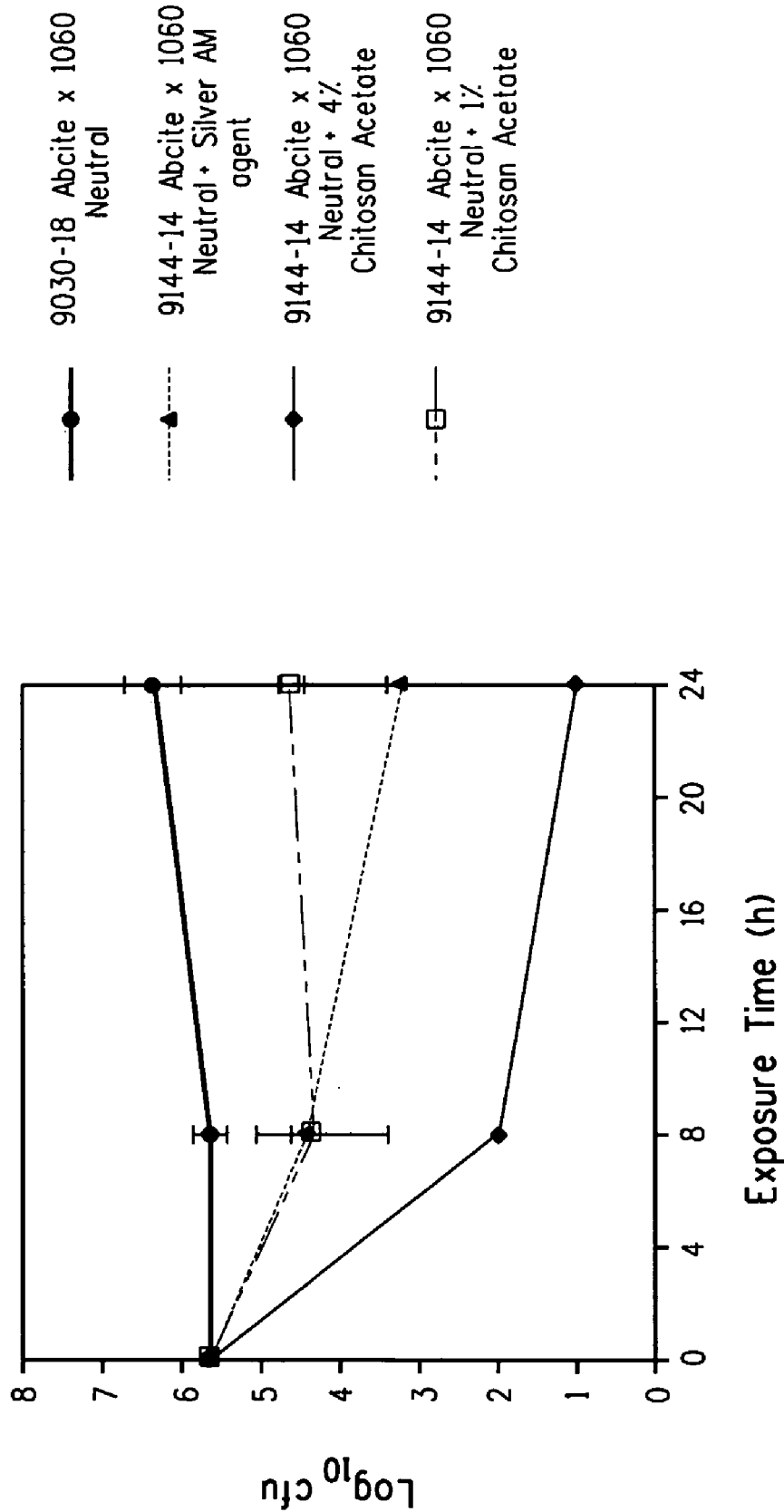
FIG. 3 is a graph that shows the effect of Abcite® coated surface on *Listeria monocytogenes* Scott A.

In regards to FIG. 1-3, at 24 h, the silver containing plates exhibited a reduction in antimicrobial activity after the wash steps of about 2-log 10 units for *E. coli* 25922, and 1-log 10 units for *S. aureus* 6530 and *L. monocytogenes* Scott A.

The Abcite®-Chitosan Acetate coatings were more effective than Abcite®-Silver for the reduction of *Staphylococcus aureus*, the latter commonly known as very difficult to fight.

What is claimed is:

1. A process of preparation of an antimicrobial powder coating composition comprising the steps:
    a) transforming a natural antimicrobial agent into a salt-form and micronizing the resulting antimicrobial salt into powder,
    b) mixing at least one of the natural antimicrobial salt together with at least one amino-reactive thermoplastic binder resin,
    c) subjecting the mixture to a melt compounding process at a temperature in a range of 80 to 230° C., at a residence time period in a range of 5 to 60 seconds, using at least one co-rotating twin-screw extruder with a soft screw design having conveying elements offering a high D/d ratio and having mixing forward kneading block elements,
    d) cooling the extrudate, and
    e) micronizing into powder particles.

2. The process according to claim 1 wherein micronizing in step a) is proceed by using an attrition or an impact milling process at room temperature.

3. The process according to claim 1 wherein mixing in step b) is proceed by a dry-mixing process.

4. The process according to claim 1 wherein the D/d ratio in step c) is in the range of 1.50 to 1.55.

5. The process according to claim 1 wherein the amount of the amino-reactive thermoplastic binder resin is in the range of 70 to 99.9 wt %, based on the total weight of the powder coating composition.

6. The process according to claim 1 wherein the amino-reactive thermoplastic binder resin is selected from the group consisting of ethylene (meth)acrylic acid, ethylene (meth)acrylate and ethylene vinyl acetate.

7. The process according to claim 1 wherein the amount of the natural antimicrobial agent is in the range of 0.1 to 20 wt %, based on the total weight of the powder coating composition.

8. The process according to claim 1 wherein the natural antimicrobial agent is selected from the group consisting of chinokitiol, chitin, chitosan, olive leaf extract.

9. A process of coating substrates applying the antimicrobial powder coating composition prepared by the process according to claim 1 onto metallic substrates and curing.

10. The process of coating substrates according to claim 9 wherein the antimicrobial powder coating composition is applied to the substrate surface as a mono-layer coating.

* * * * *